United States Patent
Hitomi et al.

(10) Patent No.: US 10,973,740 B2
(45) Date of Patent: Apr. 13, 2021

(54) POWDER-LIQUID TYPE DENTURE BASE LINING MATERIAL

(71) Applicant: TOKUYAMA DENTAL CORPORATION, Tokyo (JP)

(72) Inventors: Miki Hitomi, Tokyo (JP); Ayumu Gyakushi, Tokyo (JP); Kei Nakashima, Tokyo (JP)

(73) Assignee: TOKUYAMA DENTAL CORPORATION, Tokyo (JP)

( * ) Notice: Subject to any disclaimer, the term of this patent is extended or adjusted under 35 U.S.C. 154(b) by 0 days.

(21) Appl. No.: 16/318,610

(22) PCT Filed: Jul. 20, 2017

(86) PCT No.: PCT/JP2017/026339
§ 371 (c)(1),
(2) Date: Jan. 17, 2019

(87) PCT Pub. No.: WO2018/016602
PCT Pub. Date: Jan. 25, 2018

(65) Prior Publication Data
US 2019/0216689 A1 Jul. 18, 2019

(30) Foreign Application Priority Data
Jul. 20, 2016 (JP) .............................. JP2016-142512

(51) Int. Cl.
| | | |
|---|---|---|
| *A61K 6/887* | (2020.01) | |
| *A61K 6/35* | (2020.01) | |
| *A61K 6/20* | (2020.01) | |
| *A61K 6/00* | (2020.01) | |
| *A61K 6/60* | (2020.01) | |
| *A61K 6/831* | (2020.01) | |

(52) U.S. Cl.
CPC .................. *A61K 6/20* (2020.01); *A61K 6/00* (2013.01); *A61K 6/60* (2020.01); *A61K 6/831* (2020.01); *A61K 6/887* (2020.01); *A61K 6/35* (2020.01)

(58) Field of Classification Search
CPC ........................................................ A61K 6/35
See application file for complete search history.

(56) References Cited

U.S. PATENT DOCUMENTS

| | | |
|---|---|---|
| 5,407,973 A | 4/1995 | Hasegawa et al. |
| 2002/0058727 A1* | 5/2002 | Nakayama ............ C08F 265/06 523/120 |
| 2015/0038614 A1 | 2/2015 | Sato et al. |

FOREIGN PATENT DOCUMENTS

| | | |
|---|---|---|
| JP | H06-219919 A | 8/1994 |
| JP | H11-071220 A | 3/1999 |
| JP | H11-335222 A | 12/1999 |
| JP | 2000-007518 A | 1/2000 |
| JP | 2006-124412 A | 5/2006 |
| WO | 2013/133280 A1 | 9/2013 |

OTHER PUBLICATIONS

Ohyama, "Study on Polymerization of PMMA/MMA Resin Initiated by BPO/amine System", The Journal of the Japanese Society for Dental Materials and Devices, vol. 21, No. 1, pp. 62-71, 2002.
International Search Report dated Sep. 1, 2017, dated Sep. 12, 2017.
English International Search Report dated Sep. 1, 2017, dated Sep. 12, 2017.

* cited by examiner

*Primary Examiner* — Michael F Pepitone
(74) *Attorney, Agent, or Firm* — Norris McLaughlin, P.A.

(57) ABSTRACT

The present invention provides a powder-liquid type denture base liner comprising: a powder material including (A) uncrosslinked resin particles, (B) an organic peroxide, (C) a pyrimidine trione derivative, and (D) an organic metal compound; and a liquid material including (E) a radical polymerizable monomer and (F) an aromatic amine compound, wherein the powder-liquid denture base liner is characterized in that the (C) pyrimidine trione derivative is 0.0002-1.0 mass parts per 100 mass parts of (E) radical polymerizable monomer.

4 Claims, No Drawings

POWDER-LIQUID TYPE DENTURE BASE LINING MATERIAL

This application is a 371 application of PCT/JP2017/026339 filed Jul. 20, 2017, which claims foreign priority benefits under 35 U.S.C. § 119 of Japanese Application Nos. 2016-142512 filed Jul. 20, 2016, the disclosures of each of which are incorporated by reference herein in their entirety.

TECHNICAL FIELD

The present invention relates to a powder-liquid type denture base lining material having excellent curability of the surface and excellent manipulability as a denture base lining material.

BACKGROUND ART

A powder-liquid type denture base lining material is a material used for repairing a denture that has become unfit for the oral mucosa of a patient through long-term use and mending the denture into a reusable state. Generally, a powder-liquid type denture base lining material is composed of a liquid material including a radical polymerizable monomer as a main component and a powder material including, as a main component, a non-crosslinked resin that is soluble in the liquid material, and a mechanism by which the two materials are mixed and then a radical polymerization initiator comes into action is applicable thereto. Examples of the radical polymerization initiator include a chemical polymerization initiator (normal temperature Redox initiator), a photopolymerization initiator, and a thermal polymerization initiator.

The powder-liquid type denture base lining material is used after being cured outside the oral cavity or after being cured directly inside the oral cavity; however, the powder-liquid type denture base lining material is frequently used by a technique that involves inserting the material is inserted directly into the oral cavity of a patient, fitting the material to an oral mucosal surface, and then polymerizing and curing the material while being retained inside the oral cavity to perform mending. Therefore, a chemical polymerization initiator is generally used as the radical polymerization initiator.

Regarding the chemical polymerization initiator, a combination of an organic peroxide and an aromatic amine compound has been widely used as the radical polymerization initiator for powder-liquid type denture base lining materials (see Non Patent Literature 1).

An advantage of a powder-liquid type denture base lining material obtained by using a chemical polymerization initiator including a combination of the organic peroxide/aromatic amine compound as a radical polymerization initiator, may be the unique change over time in the viscosity of the material. That is, in such a powder-liquid type denture base lining material, when a powder material and a liquid material are mixed, the non-crosslinked resin slowly swell and dissolves in the radical polymerizable monomer, and the mixture becomes a resin sludge. Therefore, immediately after mixing, the swelling and dissolution of the non-crosslinked resin component in the radical polymerizable monomer component occurs to a less extent, and the sludge is highly flowable; however, as the radical polymerizable monomer component further penetrates into the non-crosslinked resin component, swelling and dissolution proceed, and the viscosity increases. Thus, the mixture goes through a state that allows plastic deformation and then is brought into a state that does not allow plastic deformation. Since the radical polymerization initiator is mixed in simultaneously with the mixing of the powder material and the liquid material, radicals are generated, and thus, the material has a function in which polymerization and curing proceed after a lapse of a predetermined period of time from the mixing.

Furthermore, a powder-liquid type denture base lining material using a chemical polymerization initiator is used by a procedure including: 1) an operation of placing a denture base lining material on the mucosal surface of a denture base; 2) an operation of inserting the denture base lining material into the oral cavity of a patient and shaping the denture base lining material; furthermore, when there is a risk that the denture base may become unremovable if the lining material is cured directly, due to the presence of undercuts or the like, 3) an operation of performing a removal adjustment from the inside of the oral cavity of the patient; and subsequently, 4) final curing. Here, at the time of carrying out the 2) operation of inserting the denture base into the oral cavity of the patient and shaping the lining material, when shaping is attempted in a state of having low viscosity, a sufficient thickness cannot be secured. In contrast, when the viscosity increases too high, conformity to the mucosal surface cannot be obtained. Furthermore, when the 3) operation of performing a removal adjustment from the inside of the oral cavity of the patient, which is an optional operation, is carried out, the removal from the inside of the oral cavity is carried out after the denture base lining material is brought into a state in which even though the lining material is removed at a higher viscosity than the viscosity at the time of shaping, the lining material does not undergo plastic deformation. Therefore, in a powder-liquid type denture base lining material used for the repair of a denture, the affinity between the powder and the liquid in the early stage of mixing, as well as the rate of viscosity increase of the resin sludge, and the manipulability to the state of final curing are considered important.

The operation of 4) final curing, that is, polymerization operation, may be performed outside the oral cavity. In a case in which the polymerization operation is performed outside the oral cavity, the surface of the cured composition is exposed to air, and an unpolymerized layer (surface unpolymerized layer) is produced. This is because at the air-exposed surface of a curable material, oxygen in air is bonded to the curable material and thereby inhibits the progress of polymerization.

When these surface unpolymerized layers are present, a decrease in the surface hardness or colorability occurs. Furthermore, in a case in which the denture base lining material has a surface unpolymerized layer, when polishing and cutting of the cured polymer are performed, the surface unpolymerized layer becomes entangled with the polishing bar, and thereby polishability is deteriorated.

In regard to the organic peroxide/aromatic amine compound-based chemical polymerization initiators that are currently widely used for powder-liquid type denture base lining materials, it has been considered that nothing can be the surface unpolymerized layer produced after curing and problems associated therewith are unavoidable.

Regarding the chemical polymerization initiators that are widely used for dental materials, combinations of a pyrimidinetrione derivative, an organic halogen compound, and an organometallic compound (these are also referred to as pyrimidinetrione-based polymerization initiators) are known in addition to the above-mentioned organic peroxide/aromatic amine compound-based chemical polymerization initiators.

In a pyrimidinetrione-based polymerization initiator, hydrogen atoms of the pyrimidinetrione derivative are extracted by the organometallic compound, and a radical species is produced. Furthermore, this radical species reacts with oxygen in air as under a catalytic action of the organic halogen compound, and as the result, a radical species in which oxygen is bonded to the 5-position carbon of the pyrimidinetrione derivative is produced. Such two radical species produced from a pyrimidinetrione derivative serve as points of initiation, and thereby, radical polymerization of radical polymerizable monomers happens to proceed.

Since oxygen is used as a trigger of a reaction, even if the polymerization operation is carried out in air, a cured product having satisfactory curability of the surface and having a diminished surface unpolymerized layer is obtained.

In Patent Literature 1, a normal temperature polymerized resin for dental use having enhanced curing characteristics has been suggested, the resin being obtained by incorporating a pyrimidinetrione derivative, an organometallic compound, a quaternary halogenated ammonium compound as an organic halogen compound, and an aromatic tertiary amine as an aromatic amine compound into a catalyst system without including an organic peroxide. However, when this catalyst system is used for a powder-liquid type denture base lining material, the surface unpolymerized layer is decreased; however, there is a defect that the curing time is short, and a desired viscosity increase as required from a denture base lining material may not be obtained.

Furthermore, in Patent Literature 2, a composition for a normal temperature polymerized resin for dental use has been suggested, which is obtained by using a pyrimidinetrione derivative, a halogen ion-forming compound as an organic halogen compound, and a cupric ion-forming compound as an organometallic compound in the catalyst system without including an organic peroxide and an aromatic tertiary amine, and further incorporating 2,4-diphenyl-4-methyl-1-pentene, the resin composition capable of producing a cured product having satisfactory physical properties and having appropriate controllability for the curing time. However, in the present embodiment the surface unpolymerized layer is decreased, and there is no problem with the curing time for the composition to be used as a denture base lining material; however, there is a defect that a sufficient time cannot be secured for the shaping operation and the removal operation, which are important for a denture base lining material, and a viscosity increase required from a denture base lining material is not obtained.

In Patent Literature 3, a powder-liquid type curable material kit for dental use has been suggested as a normal temperature polymerized resin for dental use, the curable material kit including a pyrimidinetrione compound as a pyrimidinetrione derivative, an organic halogen compound, an organometallic compound, and an organic peroxide in combination in the catalyst system without including an aromatic tertiary amine, for which heat generation upon curing can be reduced, and excessive prolongation of the curing time is not likely to occur even through a brush-on technique. However, although the mixing ratio of those pyrimidinetrione derivative and organic peroxide is described, when the catalyst system is used for a powder-liquid type denture base lining material, the amount of incorporation of the pyrimidinetrione derivative is large, and the surface unpolymerized layer is decreased. However, there is a defect that the curing time is short, and a desired viscosity increase as required from a denture base lining material may not be obtained.

Under such circumstances, there has been a strong demand for the development of a powder-liquid type denture base lining material that exhibits a diminished surface unpolymerized layer, enhanced curability, a desired viscosity increase as required from a denture base lining material, and excellent manipulability.

CITATION LIST

Patent Literature

Patent Literature 1: JP H06-219919 A
Patent Literature 2: JP H11-071220 A
Patent Literature 3: WO 2013/133280 A Non Patent Literature Non Patent Literature 1: The Journal of the Japanese Society for Dental Materials and Devices, Vol. 21, No. 1, 62-71, 2002

SUMMARY OF INVENTION

Technical Problem

Therefore, an object of the present invention provides a powder-liquid type denture base lining material that exhibits a diminished surface unpolymerized layer, enhanced curability, a desired viscosity increase as required from a denture base lining material, and excellent manipulability.

Solution to Problem

The inventors of the present invention repeatedly conducted thorough investigations in order to solve the problems described above, and as a result, the inventors found that when an organic peroxide, an aromatic amine compound, a pyrimidinetrione derivative, and an organometallic compound are included as radical polymerization initiators for a powder-liquid type denture base lining material, and an extremely small amount of a pyrimidinetrione derivative is incorporated into the powder-liquid type denture base lining material, a powder-liquid type denture base lining material that exhibits a diminished surface unpolymerized layer, enhanced curability, a desired viscosity increase as required from a denture base lining material, and excellent manipulability, can be obtained. Thus, the inventors completed the present invention.

That is, the present invention provides
a powder-liquid type denture base lining material including a powder material including: (A) non-crosslinked resin particles, (B) an organic peroxide, (C) a pyrimidinetrione derivative, and (D) an organometallic compound; and
a liquid material including: (E) a radical polymerizable monomer, and (F) an aromatic amine compound,
in which the (C) pyrimidinetrione derivative is included in an amount of 0.0002 to 1.0 part by mass with respect to 100 parts by mass of the (E) radical polymerizable monomer.

The powder-liquid type denture base lining material of the present invention is preferably such that:
(1) the (B) organic peroxide is incorporated in an amount of 0.2 to 10 parts by mass, and the (D) organometallic compound is incorporated in an amount of 0.000002 to 0.1 part by mass, with respect to 100 parts by mass of the (E) radical polymerizable monomer;
(2) the mass ratio of the (C) pyrimidinetrione derivative to the (B) organic peroxide is 0.001 to 0.1;

(3) 0.5 part by mass or less of the (G) organic halogen compound is incorporated into the liquid material with respect to 100 parts by mass of the radical polymerizable monomer;

(4) the molecular weight of the (E) radical polymerizable monomer is 150 or greater; and (5) the (C) pyrimidinetrione derivative is a compound represented by the following General Formula (1):

[Chemical Formula 1]

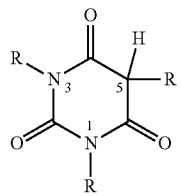

(1)

wherein under the condition that all of three R's are not hydrogen atoms, three R's each represent a hydrogen atom, an alkyl group having 1 to 8 carbon atoms, or a cycloalkyl group having 3 to 8 carbon atoms.

Advantageous Effects of Invention

The powder-liquid type denture base lining material of the present invention includes an organic peroxide, an aromatic amine compound, a pyrimidinetrione derivative, and an organometallic compound as radical polymerization initiators, and by incorporating an extremely small amount of a pyrimidinetrione derivative, a powder-liquid type denture base lining material that exhibits a diminished surface unpolymerized layer, enhanced curability, a desired viscosity increase as required from a denture base lining material, and excellent manipulability can be provided.

The reasons for the present effect are not clearly understood; however, the inventors of the present invention consider the reasons as follows.

That is, as described above, in regard to a pyrimidinetrione-based polymerization initiator, hydrogen atoms of a pyrimidinetrione derivative are extracted by an organometallic compound, and a radical species is produced. Furthermore, this radical species reacts with oxygen in air under the catalytic action of an organic halogen compound, and as the result, a radical species having oxygen bonded to the 5-position carbon of the pyrimidinetrione derivative is produced. Such two radical species produced from a pyrimidinetrione derivative serve as initiation points, and thereby radical polymerization of a radical polymerizable monomer proceeds.

Since oxygen is used as a trigger for the reaction, even if the polymerization operation is carried out in air, a cured product having satisfactory curability of the surface and having a diminished surface unpolymerized layer is obtained.

In the present invention, it is speculated that by using an extremely small amount as the amount of incorporation of a pyrimidinetrione derivative, a cured product having enhanced curability of the surface and a diminished surface unpolymerized layer is obtained; however, after all, the pyrimidinetrione derivative does not affect polymerization and curing accompanied by unique changes over time in the viscosity caused by a combination of an organic peroxide and an aromatic amine compound, and appropriate viscosity increase is maintained, so that excellent manipulability as required from a powder-liquid type denture base lining material is obtained.

In addition, the powder-liquid type denture base lining material of the present invention uses an organic peroxide and an aromatic amine compound as radical polymerization initiators, and further uses a pyrimidinetrione derivative and an organometallic compound; however, it was found that even if the lining material does not include an organic halogen compound, which has been hitherto used as an essential pyrimidinetrione-based polymerization initiator, curability of the surface is enhanced. Regarding the reason for this, it is considered to be because the role played by an organic halogen compound in a conventional pyrimidinetrione-based polymerization initiator is played instead by an aromatic amine compound.

Furthermore, in a case in which an organic halogen compound is not incorporated, solubility in a polymerizable monomer is increased, the production time for the liquid is shortened to a large extent, and productivity is enhanced.

DESCRIPTION OF EMBODIMENTS

The powder-liquid type denture base lining material of the present invention includes a powder material including: (A) non-crosslinked resin particles, (B) an organic peroxide, (C) a pyrimidinetrione derivative, and (D) an organometallic compound; as well as (E) a radical polymerizable monomer, and (F) an aromatic amine compound.

In the following description, various constituent components will be described separately.

<(A) Non-Crosslinked Resin Particles>

In regard to the powder-liquid type denture base lining material of the present invention, the non-crosslinked resin particles constitute a main component of the powder material, and these particles refer to non-crosslinked resin particles having solubility in the (E) radical polymerizable monomer, which is a main component of the liquid material that will be described below. When the powder material and the liquid material are mixed, at least a portion of such non-crosslinked resin particles dissolves in the liquid material, and as the particles of dissolution residue swell, the mixture is thickened. Thus, the polymerizability of the (E) radical polymerizable monomer described below is promoted. In addition, the particles of dissolution residue of this component also have an effect of increasing toughness of a cured product of the denture base lining material.

Here, the non-crosslinked resin particles that are soluble in the (E) radical polymerizable monomer imply that when 200 parts by mass of these non-crosslinked resin particles are mixed with 100 parts by mass of the (E) radical polymerizable monomer at 23 C, and the mixture is stirred, the non-crosslinked resin particles can dissolve in the (E) radical polymerizable monomer described below in an amount of 10 parts by mass or more.

Regarding such non-crosslinked resin particles that are soluble in the (E) radical polymerizable monomer as a main component of the liquid material, any known synthetic resin or natural resin having such characteristics can be used without any limitations. A resin having a refractive index in the range of 1.4 to 1.7, which is useful for dental use, can be suitably used. Examples of the non-crosslinked resin that constitute particles include (meth)acrylates such as polymethyl methacrylate, polyethyl methacrylate, and a copolymer of methyl methacrylate and ethyl methacrylate; polyethylene, polypropylene, polyamides, polyesters, and polystyrenes. Among these, from the viewpoint that the cured product has high toughness, polymers of lower alkyl (alkyl chain having four or fewer carbon atoms) (meth)acrylate-based polymerizable monomers, such as polymethyl methacrylate, polyethyl methacrylate, and a copolymer of methyl methacrylate and ethyl methacrylate are particularly preferred, and these may be used singly or in combination of two or more kinds thereof.

The average particle size of these non-crosslinked resin particles obtainable from the D50 value of the volume percentage measured using a laser diffraction/scattering type particle size distribution apparatus based on Mie scattering theory is not particularly limited; however, when good affinity with the radical polymerizable monomer is considered, the average particle size is preferably 200 m or less, and particularly preferably 1 to 100 m. Furthermore, the shape of the non-crosslinked resin particles is not particularly limited, and the shape may be a spherical shape, an irregular shape, or an undefined shape.

Regarding a suitable weight average molecular weight according to the Gel Permeation Chromatography (GPC) method of the non-crosslinked resin particles, when the mechanical strength of the cured product thus obtainable or the solubility, swelling or the like in the radical polymerizable monomer component are considered, the weight average molecular weight is preferably in the range of 30,000 to 2,000,000, and particularly preferably in the range of 50,000 to 1,500,000.

The amount of incorporation of these non-crosslinked resin particles is preferably 30 to 450 parts by mass with respect to 100 parts by mass of the (E) radical polymerizable monomer, and it is preferable that the non-crosslinked resin particles are incorporated particularly in an amount in the range of 80 to 350 parts by mass, and most suitably in the range of 130 to 300 parts by mass.

<(B) Organic Peroxide>

Regarding the organic peroxide used for the powder-liquid type denture base lining material of the present invention, any organic peroxide capable of generating a radical by contact with (F) an aromatic amine compound that will be described below can be used without any limitations. Examples include a ketone peroxide, a peroxyketal, a hydroperoxide, a diaryl peroxide, a peroxyester, a diacyl peroxide, a peroxydicarbonate, and a hydroperoxide, and from the viewpoint of storage stability and ease of availability, a hydroperoxide and a diacyl peroxide are suitably used. Specific examples of a suitable organic peroxide include, among diacyl peroxides, benzoyl peroxide, 2,4-dichlorobenzoyl peroxide, and lauroyl peroxide; and among hydroperoxides, 1,1,3,3-tetramethylbutyl hydroperoxide.

Suitable amounts of use of these organic peroxides vary depending on the type of the organic peroxide used and thus cannot be limited indiscriminately. However, generally, the amount of use is preferably in the range of 0.2 to 10 parts by mass, more preferably 0.35 to 7 parts by mass, and more preferably 0.5 to 5 parts by mass, with respect to 100 parts by mass of the (E) radical polymerizable monomer. For example, in the case of using benzoyl peroxide or 1,1,3,3-tetramethylbutyl hydroperoxide, the amount of use is preferably in the range of 0.2 to 10 parts by mass, more preferably 0.4 to 6 parts by mass, and even more preferably 0.6 to 4 parts by mass, with respect to 100 parts by mass of the (E) radical polymerizable monomer.

<(C) Pyrimidinetrione Derivative>

Regarding the pyrimidinetrione derivative used for the powder-liquid type denture base lining material of the present invention, known compounds are used without particular limitations.

Such a pyrimidinetrione derivative is known per se and is a compound represented by, for example, the following General Formula (1):

[Chemical Formula 2]

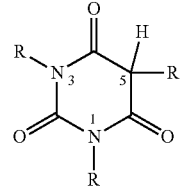

(1)

wherein under the condition that all of three R's are not hydrogen atoms, three R's each represent a hydrogen atom, an alkyl group having 1 to 8 carbon atoms, a cycloalkyl group having 3 to 8 carbon atoms, or a phenyl group.

Examples of the alkyl group having 1 to 8 carbon atoms include a methyl group, an ethyl group, an n-propyl group, an iso-propyl group, an n-butyl group, an iso-butyl group, a sec-butyl group, a tert-butyl group, a pentyl group, a hexyl group, a heptyl group, and an octyl group.

Examples of the cycloalkyl group having 3 to 8 carbon atoms include a cyclopropyl group, a cyclobutyl group, a cyclopentyl group, a cyclohexyl group, and a 3- or 4-methylcyclohexyl group.

As described above, a pyrimidinetrione-based polymerization initiator usually serves as an initiation point of two kinds of radical species generated from the pyrimidinetrione derivative, and radical polymerization of a radical polymerizable monomer proceeds therefrom. That is, in General Formula (1) described above, a hydrogen atom on the 5-position carbon atom that has been activated by a carbonyl group is extracted, and this becomes a radical initiation point.

According to the present invention, specific examples of such a pyrimidinetrione derivative include, but are not limited to, 5-methylpyrimidinetrione, 5-ethylpyrimidinetrione, 5-propylpyrimidinetrione, 5-butylpyrimidinetrione, 5-isobutylpyrimidinetrione, 1,5-dimethylpyrimidinetrione, 1,5-diethylpyrimidinetrione, 1-methyl-5-ethylpyrimidinetrione, 1-ethyl-5-methylpyrimidinetrione, 1-methyl-5-butylpyrimidinetrione, 1-ethyl-5-butylpyrimidinetrione, 1-methyl-5-isobutylpyrimidinetrione, 1-ethyl-5-isobutylpyrimidinetrione, 1-methyl-5-cyclohexylpyrimidinetrione, 1-ethyl-5-cyclohexylpyrimidinetrione, 1-benzyl-5-phenylpyrimidinetrione, 1,3,5-trimethylpyrimidinetrione, 1,3-dimethyl-5-ethylpyrimidinetrione, 1,3-dimethyl-5-butylpyrimidinetrione, 1,3-dimethyl-5-isobutylpyrimidinetrione, 1,3,5-triethylpyrimidinetrione, 1,3-diethyl-5-methylpyrimidinetrione, 1,3-diethyl-5-butylpyrimidinetrione, 1,3-diethyl-5-isobutylpyrimidinetrione, 1,3-dimethyl-5-phenylpyrimidinetrione, 1,3-diethyl-5-phenylpyrimidinetrione, 1-ethyl-3-methyl-5-butylpyrimidinetrione, 1-ethyl-3-methyl-5-isobutylpyrimidinetrione, 1-methyl-3-propyl-5-ethylpyrimidinetrione, 1-ethyl-3-propyl-5-methylpyrimidinetrione, 1-cyclohexyl-5-methylpyrimidinetrione, 1-cyclohexyl-5-ethylpyrimidinetrione, 5-butyl-1- cyclohexylpyrimidinetrione, 5-sec-butyl-1-cyclohexylpyrimidinetrione, 1-cyclohexyl-5-hexylpyrimidinetrione, 1-cyclohexyl-5-octylpyrimidinetrione, and 1,5-dicyclohexylpyrimidinetrione. These can be used singly or in combination of two or more kinds thereof.

According to the present invention, among the pyrimidinetrione derivatives described above, from the viewpoints of solubility in the (E) radical polymerizable monomer and the activity of radical polymerization, a pyrimidinetrione derivative having an alkyl group (suitably having 1 to 4 carbon atoms) or a cycloalkyl group (suitably having 3 to 6 carbon atoms) bonded to a nitrogen atom is suitable, and a pyrimidinetrione derivative having a cycloalkyl group bonded to the 1-position nitrogen atom is more suitable. From the viewpoint that hydrogen that serves as a radical initiation point is more easily extracted, a compound having an alkyl group or a cycloalkyl group bonded to the 5-position carbon atom is optimal. Regarding optimal compounds, 1-cyclohexyl-5-methylpyrimidinetrione, 1-cyclohexyl-5-ethylpyrimidinetrione, 5-butyl-1-cyclohexylpyrimidinetrione, 5-sec-butyl-1-cyclohexylpyrimidinetrione, 1-cyclohexyl-5-hexylpyrimidinetrione, 1-cyclohexyl-5-octylpyrimidinetrione, or 1,5-dicyclohexylpyrimidinetrione can be used.

The amount of incorporation of the pyrimidinetrione derivative described above is, at the time when the powder material is mixed with the liquid material, 0.0002 to 1.0 part by mass, suitably 0.0008 to 0.42 part by mass, and more suitably 0.0018 to 0.2 part by mass, with respect to 100 parts by mass of the (E) radical polymerizable monomer in the mixture.

When the amount of incorporation of the pyrimidinetrione derivative is less than 0.0002 part by mass, since the effect of preventing the inhibition of polymerization by oxygen is low, a surface unpolymerized layer is produced in the cured product, and an improvement in the curability of the surface of the cured product cannot be expected. Furthermore, when the amount of incorporation is larger than 1.0 part by mass, since the progress of polymerization and curing is fast, the viscosity increase is fast, and there is a possibility that a desired viscosity increase as required from a denture base lining material may not be obtained.

A desired viscosity increase as required from a denture base lining material is represented by the time required for the complex modulus to change from $10^3$ Pa to $10^4$ Pa, or the time required for the complex modulus to change from $10^4$ Pa to $10^6$ Pa (these are described as the $10^3$ Pa to $10^4$ Pa complex modulus retention time and the $10^4$ Pa to $10^6$ Pa complex modulus retention time, respectively).

From a clinical view, a state in which the complex modulus of a paste obtainable by mixing the powder material and the liquid material is about $10^3$ Pa to $10^4$ Pa is appropriate for the stage of inserting into the oral cavity and shaping.

The $10^3$ Pa to $10^4$ Pa complex modulus retention time is preferably 30 to 150 seconds, more preferably 30 to 120 seconds, and most preferably 30 to 90 seconds.

When this complex modulus retention time is shorter than 30 seconds, the operation time for performing shaping can be sufficiently secured. The upper limit is not necessarily limited; however, from the viewpoint of shortening the operation time, the retention time is preferably 150 seconds or shorter.

Furthermore, a state in which the complex modulus of the paste obtainable by mixing the powder material and the liquid material is about $10^4$ Pa to $10^6$ Pa is appropriate for the stage of taking out from the oral cavity and performing trimming.

The $10^4$ Pa to $10^6$ Pa complex modulus retention time is preferably 60 to 360 seconds, more preferably 60 to 300 seconds, and most preferably 60 to 180 seconds.

When this complex modulus retention time is shorter than 60 seconds, the operation time for performing trimming can be sufficiently secured. The upper limit is not necessarily limited; however, from the viewpoint of shortening the opening time, the retention time is preferably 360 seconds or shorter.

It may be redundant to say, but the feature of the present invention is to provide a powder-liquid type denture base lining material including an organic peroxide, an aromatic amine compound, a pyrimidinetrione derivative, and an organometallic compound as radical polymerization initiators, the powder-liquid type denture base lining material exhibiting, by having an extremely small amount of a pyrimidinetrione derivative incorporated therein, a unique viscosity increase provided by a combination of organic peroxide/aromatic amine compound as a denture base lining material and having a diminished surface unpolymerized layer and excellent curability while maintaining excellent manipulability.

The behavior for viscosity increase of the present invention is affected by non-crosslinked resin particles, a radical polymerizable monomer, an organic peroxide, an aromatic amine compound, and a pyrimidinetrione derivative. That is, the behavior for viscosity increase is affected in a complex manner by the dissolution/swelling/thickening of the (A) non-crosslinked resin particles in the (E) radical polymerizable monomer; a polymerization reaction induced by the (B) organic peroxide and the (F) aromatic amine compound; and a polymerization reaction induced by the (C) pyrimidinetrione derivative. Therefore, it is not preferable that the denture base lining material includes any substance inhibiting the action provided by such a combination of these components.

Therefore, the complex modulus retention time can be adjusted by arbitrarily changing the type or amount of incorporation of those components; however, when the amount of incorporation of the (C) pyrimidinetrione derivative is larger than 1.0 part by mass, the progress of polymerization and curing brought by the pyrimidinetrione-based polymerization initiator is fast, the viscosity increase is accelerated all at once to an uncontrollable level. As a result, the $10^3$ Pa to $10^4$ Pa complex modulus retention time becomes shorter than 30 seconds, and the $10^4$ Pa to $10^6$ Pa complex modulus retention time becomes shorter than 60 seconds, so that there is a possibility that a desired viscosity as required from a denture base lining material may not be obtained.

Furthermore, it is preferable that the amount of incorporation of the (C) pyrimidinetrione derivative with respect to the (B) organic peroxide is also adjusted to an extremely small amount. That is, in a case in which the amount of incorporation of the pyrimidinetrione derivative with respect to the organic peroxide is also adjusted to an extremely small amount, the surface unpolymerized layer can be diminished, and the effect of the present invention that a desired viscosity increase as required from a denture base lining material may be obtained becomes superior.

The mass ratio of the (C) pyrimidinetrione derivative to the (B) organic peroxide is preferably 0.001 to 0.1, particularly preferably 0.002 to 0.07, and most suitably 0.003 to 0.05.

<(D) Organometallic Compound>

Regarding the organometallic compound used for the powder-liquid type denture base lining material of the present invention, any conventionally known compound that is used for a pyrimidinetrione-based polymerization initiator can be used. Specific examples thereof that can be used include, but are not limited to, copper(II) compounds such as acetylacetone copper(II), copper(II) 4-cyclohexylbutyrate, copper(II) acetate, and copper(II) oleate; manganese compounds such as acetylacetone manganese, manganese naphthenate, and manganese octoate; cobalt compounds such as acetylacetone cobalt and cobalt naphthenate; lithium compounds such as acetylacetone lithium and lithium acetate; zinc compounds such as acetylacetone zinc and zinc naphthenate; nickel compounds such as acetylacetone nickel and nickel acetate; aluminum compounds such as acetylacetone aluminum; calcium compounds such as acetylacetone calcium; iron (II) compounds such as acetylacetone iron (II); and other compounds such as acetylacetone chromium, sodium naphthenate, and rare earth octoates. These can be used singly or in combination of two or more kinds thereof.

Among the organometallic compounds described above, from the viewpoint of polymerization activity, copper(II) compounds or iron(II) compounds are preferred, and acetylacetone copper(II), copper(II) acetate, copper(II) oleate, and acetylacetone iron(II) are particularly preferred.

According to the present invention, it is preferable that the organometallic compound is incorporated so as to exist in an amount of 0.000002 to 0.1 part by mass, particularly 0.00001 to 0.04 part by mass, and most suitably 0.00002 to 0.02 part by mass, with respect to 100 parts by mass of the (E) radical polymerizable monomer, from the viewpoint of enhancing satisfactory curability of the surface. When the amount of incorporation of this organometallic compound is less than 0.000002 part by mass, since the effect of preventing the inhibition of polymerization by oxygen is low, an enhancement of the curability of the cured product surface cannot be expected. Furthermore, when the amount of incorporation is larger than 0.1 part by mass, the viscosity increase occurs rapidly, and there is a possibility that a desired viscosity increase as required from a denture base lining material may not be obtained. This is causative of coloration or discoloration of the cured product.

<(E) Radical Polymerizable Monomer>

Regarding the (E) radical polymerizable monomer used for the powder-liquid type denture base lining material of the present invention, any radical polymerizable monomer that can be used for dental use can be used without any particular limitations, and any known compound can be used without any particular limitations. The radical polymerizable monomer may be a radical polymerizable monomer having a radical polymerizable group such as a vinyl group or a styryl group; however, from the viewpoint of having satisfactory polymerizability, a (meth)acrylate-based polymerizable monomer is suitably used.

Regarding the (meth)acrylate-based polymerizable monomer, any known compound that is generally used for dental use is used without any particular limitations, and low-molecular weight (meth)acrylate-based polymerizable monomers such as methyl (meth)acrylate, ethyl (meth)acrylate, propyl (meth)acrylate, butyl (meth)acrylate, isopropyl (meth)acrylate, hydroxyethyl (meth)acrylate, and methoxyethylene glycol (meth)acrylate may be used. However, from the viewpoint of being a material having high mechanical strength and less irritancy, it is preferable to incorporate a radical polymerizable monomer having a molecular weight of 150 or more, and more suitably 180 or more. As monofunctional monomers, specific preferred examples of a (meth)acrylate-based polymerizable monomer having a molecular weight of 150 or more include n-hexyl (meth)acrylate, cyclohexyl (meth)acrylate, tetrahydrofurfuryl (meth)acrylate, dimethylaminoethyl (meth)acrylate, n-octadecyl (meth)acrylate, n-dodecyl (meth)acrylate, n-tridecyl (meth)acrylate, 2-(meth)acryloxyethyl propionate, ethoxyethylene glycol (meth)acrylate, acetoacetoxyethyl (meth)acrylate, acetoacetoxypropyl (meth)acrylate, acetoacetoxybutyl (meth)acrylate, and diethylaminoethyl (meth)acrylate. Among these, more suitable examples of a (meth)acrylate-based polymerizable monomer having a molecular weight of 180 or more include n-octadecyl (meth)acrylate, n-dodecyl (meth)acrylate, n-tridecyl (meth)acrylate, 2-(meth)acryloxyethyl propionate, ethoxyethylene glycol (meth)acrylate, acetoacetoxyethyl (meth)acrylate, acetoacetoxypropyl (meth)acrylate, acetoacetoxybutyl (meth)acrylate, and diethylaminoethyl (meth)acrylate.

Furthermore, regarding the radical polymerizable monomer, the above-mentioned monofunctional monomers may be used singly, or the monofunctional monomers may be each used in combination with a polyfunctional polymerizable monomer. Examples of the polyfunctional polymerizable monomer include a bifunctional polymerizable monomer, a trifunctional polymerizable monomer, and a tetrafunctional polymerizable monomer.

As bifunctional monomers, specific examples of a (meth)acrylate-based polymerizable monomer having a molecular weight of 180 or more include ethylene glycol di(meth)acrylate, diethylene glycol di(meth)acrylate, triethylene glycol di(meth)acrylate, tetraethylene glycol di(meth)acrylate, pentaethylene glycol di(meth)acrylate, hexaethylene glycol di(meth)acrylate, octaethylene glycol di(meth)acrylate, nonaethylene glycol di(meth)acrylate, decaethylene glycol di(meth)acrylate, undecaethylene glycol di(meth)acrylate, dodecaethylene glycol di(meth)acrylate, tridecaethylene glycol di(meth)acrylate, tetradecaethylene glycol di(meth)acrylate, pentadecaethylene glycol di(meth)acrylate, hexadecaethylene glycol di(meth)acrylate, heptadecaethylene glycol di(meth)acrylate, octadecaethylene glycol di(meth)acrylate, nonadecaethylene glycol di(meth)acrylate, eicosaethylene glycol di(meth)acrylate, heneicosaethylene glycol di(meth)acrylate, docosaethylene glycol di(meth)acrylate, tricosaethylene glycol di(meth)acrylate, tetracosaethylene glycol di(meth)acrylate, pentacosaethylene glycol di(meth)acrylate, hexacosaethylene glycol di(meth)acrylate, propylene glycol di(meth)acrylate, butylene glycol di(meth)acrylate, neopentyl glycol di(meth)acrylate, 1,3-butanediol di(meth)acrylate, 1,4-butanediol di(meth)acrylate, 1,6-hexanediol di(meth)acrylate, 1,9-nonanediol di(meth)acrylate, 1,10-decanediol di(meth)acrylate, 1,12-stearyl di(meth)acrylate, 2,2-bis((meth)acryloxyphenyl)propane, 2,2-bis[4-(2-hydroxy-3-(meth)acryloxyphenyl)]propane, 2,2-bis(4-(meth)acryloxyethoxyphenyl)propane, 2,2-bis(4-(meth)acryloxydiethoxyphenyl)propane, and 2,2-bis(4-(meth)acryloxypropoxyphenyl)propane.

As trifunctional monomers, specific examples of a (meth)acrylate-based polymerizable monomer having a molecular weight of 180 or more include trimethylolpropane tri(meth)acrylate, pentaerythritol tri(meth)acrylate, and trimethylolmethane tri(meth)acrylate.

As tetrafunctional monomers, specific examples of a (meth)acrylate-based polymerizable monomer having a molecular weight of 180 or more include pentaerythritol tetra(meth)acrylate.

<(F) Aromatic Amine Compound>

The aromatic amine compound used for the powder-liquid type denture base lining material of the present invention is a compound capable of generating a radical by contacting with the organic peroxide described above. Regarding the aromatic amine compound, any known compound that is used as a chemical polymerization catalyst in combination with an organic peroxide is used without any particular limitations, and from the viewpoint of having an excellent ability to decompose an organic peroxide that serves as polymerization initiation and thereby accelerating polymerization, an aromatic tertiary amine compound is suitably used.

Specific examples of an aromatic amine compound that is suitably used include anilines such as N,N-dimethylaniline, N,N-diethylaniline, N,N-dipropylaniline, N,N-dibutylaniline, N-methyl, N-hydroxyethylaniline; toluidines such as N,N-dimethyl-p-toluidine, N,N-diethyl-p-toluidine, N,N-dipropyl-p-toluidine, N,N-dibutyl-p-toluidine, p-tolyldiethanolamine, and p-tolyldipropanolamine; anisidines such as N,N-dimethyl-anisidine, N,N-diethyl-p-anisidine, N,N-dipropyl-p-anisidine, N,N-dibutyl-p-anisidine; morpholines such as N-phenylmorpholine; bis(N,N-dimethylaminophenyl)methane, and bis(N,N-dimethylaminophenyl) ether. These aromatic amine compounds may also be used as salts with hydrochloric acid, phosphoric acid, or an organic acid such as acetic acid or propionic acid.

Among the above-mentioned aromatic amine compounds, from the viewpoint of having high polymerization activity and being less irritant and less odorous, N,N-dimethyl-p-toluidine, N,N-diethyl-p-toluidine, N,N-dipropyl-p-toluidine, p-tolyldiethanolamine, and p-tolyldipropanolamine are suitably used. Furthermore, in a case in which long-term storage of the aromatic amine compound in a state of being mixed with a radical polymerizable monomer is needed, it is preferable to use N,N-dimethyl-p-toluidine, N,N-diethyl-p-toluidine, or p-tolyldiethanolamine, from the viewpoint of storage stability.

The amount of use of the aromatic amine compound is preferably 0.1 to 5 parts by mass, more preferably 0.2 to 3 parts by mass, and even more preferably in the range of 0.3 to 2 parts by mass, with respect to 100 parts by mass of the (E) radical polymerizable monomer.

Furthermore, the mass ratio of the (F) aromatic amine compound to the (B) organic peroxide is not particularly limited; however, it is preferable that the (F) aromatic amine compound exists at a mass ratio of generally 0.03 to 4, particularly preferably 0.08 to 2, and most suitably 0.15 to 1.5.

Among the combinations of the (B) organic peroxide and the aromatic amine compound, specific suitable examples include combinations of benzoyl peroxide/N,N-dimethyl-p-toluidine, benzoyl peroxide/N,N-diethyl-p-toluidine, benzoyl peroxide/N,N-dipropyl-p-toluidine, benzoyl peroxide/p-tolyldiethanolamine, benzoyl peroxide/p-tolyldipropanolamine, and 1,1,3,3-tetramethylbutyl hydroperoxide/N,N-dimethyl-p-toluidine.

Among them, in a case in which long-term storage of the aromatic amine compound in a state of being mixed with a radical polymerizable monomer is needed, from the viewpoint of storage stability, combinations of benzoyl peroxide/N,N-dimethyl-p-toluidine, benzoyl peroxide/N,N-diethyl-p-toluidine, benzoyl peroxide/N,N-dipropyl-p-toluidine, and benzoyl peroxide/p-tolyldiethanolamine are most preferred.

<Other Components>

In the powder-liquid type denture base lining material of the present invention, various components such as the (G) organic halogen compound that will be described below may be incorporated, as necessary, in addition to the components described above.

<(G) Organic Halogen Compound>

In the present invention, only with the (C) pyrimidinetrione derivative and the (D) organometallic compound among the pyrimidinetrione-based polymerization initiators as described above, the effect that an enhancement in the curability of the surface and a desired viscosity increase as required from a denture base lining material may be obtained is exhibited; however, (G) an organic halogen compound may be further incorporated. It is desirable that the (G) organic halogen compound may be incorporated into the liquid material.

Representative examples of the organic halogen compound that is used for the pyrimidinetrione-based polymerization initiator are quaternary halogenated ammonium compounds, and specific examples include dilauryldimethylammonium chloride, lauryldimethylbenzylammonium chloride, benzyltrimethylammonium chloride, diisobutylamine hydrochloride, tetra-n-butylammonium chloride, triethylamine hydrochloride, trimethylamine hydrochloride, dimethylamine hydrochloride, diethylamine hydrochloride, methylamine hydrochloride, ethylamine hydrochloride, isobutylamine hydrochloride, triethanolamine hydrochloride, -phenylethylamine hydrochloride, acetylcholine chloride, 2-chlorotrimethylamine hydrochloride, (2-chloroethyl)triethylammonium chloride, tetradecyldimethylbenzylammonium chloride, tetraethylammonium chloride, tetramethylammonium chloride, trioctylmethylammonium chloride, benzyldimethylcetylammonium chloride, benzyldimethylstearylammonium chloride, dilauryldimethylammonium bromide, tetrabutylammoniumbromide, and benzyltriethylammonium bromide. These organic halogen compounds can be used singly, or a plurality of kinds can be used in combination.

According to the present invention, in the case of incorporating the (G) organic halogen compound, higher polymerization activity can be obtained, and the curability of the surface can be enhanced. Particularly, from the viewpoint of enhancing the curability of the surface, it is particularly preferable to use dilauryldimethylammonium chloride or dilauryldimethylammonium bromide.

It is desirable that the (G) organic halogen compound described above is used in an amount of 0.5 part by mass or less, particularly 0.2 part by mass or less, and more suitably 0.1 part by mass or less, with respect to 100 parts by mass of the (E) radical polymerizable monomer described above. When the amount of incorporation is 0.5 part by mass or less, there is no chance that the polymerization characteristics of the pyrimidinetrione-based polymerization initiator are excessively activated and thus lead to rapid proceeding of the polymerization reaction, and a desired viscosity increase as required from a denture base lining material can be obtained. Meanwhile, since the (G) organic halogen compound requires a longtime to be dissolved in the (E) radical polymerizable monomer, and the productivity of the liquid material is markedly deteriorated, it is desirable that the amount of the (G) organic halogen compound is small from the viewpoint of enhancing the productivity of the liquid material, while it is preferable not to incorporate the (G) organic halogen compound.

Furthermore, in order to improve fluidity or to control general physical properties and manipulability of a cured product thus obtainable, an inorganic filler and an organic filler (crosslinked resin particles); an alcohol or a plasticizer, such as ethanol, dibutyl phthalate, or dioctyl phthalate; a polymerization inhibitor such as butyl hydroxytoluene or methoxyhydroquinone; an ultraviolet absorber such as 4-methoxy-2-hydroxybenzophenone or 2-(2-benzotriazole)-p-cresol; a polymerization regulating agent such as 2,4-diphenyl-4-methyl-1-pentene; a coloring material, a pigment, a fragrance, and the like can be incorporated into the powder material or the liquid material. In the case of incorporating the inorganic filler and the organic filler, these are usually incorporated into the powder material, and the total amount of incorporation is preferably suppressed to be 10 parts by mass or less with respect to 100 parts by mass of the (E) radical polymerizable monomer, and it is particularly preferable to suppress the total amount of incorporation to be 6 parts by mass or less.

Thus, the various constituent components have been separately described; however, the denture base lining material according to the present invention is a material that is composed of a powder material including (A) a non-crosslinked resin particles, (B) an organic peroxide, (C) a pyrimidinetrione derivative, and (D) an organometallic compound; and a liquid material including (E) a radical polymerizable monomer and (F) an aromatic amine compound, the powder material and the liquid material being mixed upon use.

The main component that constitutes the powder material is the (A) non-crosslinked resin particles. Here, the term main component implies that the content of the (A) non-crosslinked resin particles in the entire amount of the powder material is 80% by mass or more, and preferably 90% by mass or more.

The main component that constitutes the liquid material is the (E) radical polymerizable monomer. Here, the term main component similarly implies that the content of the (E) radical polymerizable monomer in the total amount of the liquid material is 80% by mass or more, and preferably 90% by mass or more.

The mixing ratio of the powder material and the liquid material is not particularly limited, and the mixing ratio may be determined as appropriate in consideration of the contents of the above-mentioned components included in the respective members and the desired amounts of use of the respective components at the time of mixing the liquid material and the powder material as described above. However, generally, the mixing ratio is preferably such that powder material (g)/liquid material (ml)=0.3/1 to 4.5/1, it is particularly preferable to mix the materials at a proportion of powder material (g)/liquid material (ml)=0.8/1 to 3.5/1, and it is most preferable to mix the materials at a proportion of powder material (g)/liquid material (ml)=1.3/1 to 3/1.

Meanwhile, it is desirable that the various components in the present specification are incorporated into the powder material or the liquid material so as to satisfy the respective amounts of incorporation when the powder material and the liquid material are mixed at the above-described proportion.

In regard to the method for producing the powder material and the liquid material, both of which are formed by mixing the various components described above, there are no particular limitations, and the materials may be produced according to known production methods. However, specifically, it is desirable that the components to be incorporated are each weighed in a predetermined amount, and the components are mixed until a uniform nature is obtained. There are also no particular limitations on the kneading machine that can be used for mixing, and any known kneading machine can be used. Specifically, a rocking mixer or the like may be mentioned. Furthermore, the powder material and the liquid material thus produced may be respectively stored in containers, or may be stored after being subdivided into arbitrary amounts. It is also acceptable that the powder material and the liquid material are weighed into an amount of single-time use and stored separately, or those divided portions of the powder material and the liquid material may be stored separately in containers that are accommodated in the same package.

Regarding the method of using such a powder-liquid type denture base lining material, the powder material and the liquid material may be mixed and used as appropriate according to various forms. For instance, the liquid material and the powder material may be weighed in a desired amount into a rubber cup or the like immediately before use, and the materials may be malaxated using a malaxation rod, a spatula, or the like until a uniform paste is formed.

EXAMPLES

Hereinafter, the present invention will be specifically described by way of Examples; however, the present invention is not intended to be limited to these experiment items. The abbreviations and names indicated in the Examples are as follows.

(A) Non-Crosslinked Resin Particles
PEMA1: Spherical polyethyl methacrylate particles (average particle size 35 m, weight average molecular weight 500,000)
PEMA2: Spherical polyethyl methacrylate particle (average particle size 70 m, weight average molecular weight 1,000,000)
(B) Organic Peroxide
BPO: Benzoyl peroxide
Perocta H: 1,1,3,3-Tetramethylbutyl hydroperoxide
(C) Pyrimidinetrione Derivative
cHexEt-PTO: 1-Cyclohexyl-5-ethylpyrimidinetrione
cHexMt-PTO: 1-Cyclohexyl-5-methylpyrimidinetrione
(D) Organometallic Compound
CuAcAc: Acetylacetone copper(II)
CuAc: Copper(II) acetate
(E) Radical Polymerizable Monomer
AAEM: Acetoacetoxyethyl methacrylate (molecular weight 214)
HPR: 2-(Meth)acryloxyethyl propionate (molecular weight 186)
ND: 1,9-Nonanediol di(meth)acrylate (molecular weight 296)
MMA: Methyl methacrylate (molecular weight 100)
(F) Aromatic Amine Compound
DMPT: N,N-dimethyl-p-toluidine
DEPT: p-Tolyldiethanolamine
(G) Organic Halogen Compound
DLDMACl: Dilauryldimethylammonium chloride
DLDMABr: Dilauryldimethylammonium bromide
(H) Other Components (Polymerization Regulating Agent)
MSD: 2,4-Diphenyl-4-methyl-1-pentene
(1) Measurement of Surface Unpolymerized Layer A powder material and a liquid material were introduced into a rubber cup at a proportion of powder material (g)/liquid material (ml)=2/1, and the materials were mixed for 20 seconds. Subsequently, the mixture was cast into a form made of polytetrafluoroethylene, which measured 20 mm in length, 20 mm in width, and 1 mm in thickness, and the mixture was left to stand for 10 minutes in a constant temperature bath at 37 C to cure. The thickness of the cured product was measured using a micrometer, and then the cured product was immersed in ethanol for one minute. The surface unpolymerized layer was shaved off from the surface of the cured product using a spatula. The thickness of the cured product from which the surface unpolymerized layer had been removed was measured, and the difference between the thickness of the cured product before immersing the cured product in ethanol and the thickness of the cured product after the removal with a spatula was designated as surface unpolymerized layer.

The surface unpolymerized layer is preferably 200 m or less. In a case in which the surface unpolymerized layer is larger than 200 m, when the denture base is used after repair without removing the surface unpolymerized layer, there is a possibility that inconveniences may occur, such as that the surface hardness is decreased, the denture base lining material is fractured at a site with a smaller thickness, such as denture periphery, or the colorability of the denture base lining material is decreased so that a problem with esthetics occurs. Furthermore, when polishing and cutting of the cured composition is performed in order to remove the surface unpolymerized layer, the surface unpolymerized layer is entangled with the polishing bar, and there occurs a problem that workability is deteriorated.

(2) Measurement of Curing Time

On a grass plate covered with a plastic sheet, a stainless steel ring (inner diameter 60 mm, outer diameter 67 mm, height 2 mm) was placed, and a thermocouple was disposed such that the tip of the thermocouple would be located at the center of the ring. A powder material and a liquid material were introduced into a rubber cup at a proportion of powder material (g)/liquid material (ml)=2/1, and the mixture was mixed for 20 seconds. The mixture was cast into a form and was pressure-welded with a plastic sheet and a glass plate. One minute and 30 seconds after the initiation of mixing, the mixture was placed in a water bath at 37 C, and the temperature measurement of the mixture was initiated. The time taken from the initiation of mixing to reach the highest temperature was designated as curing time.

Meanwhile, the curing time for a clinical powder-liquid type denture base lining material is suitably 3 minutes and 30 seconds to 10 minutes or less. When the curing time is shorter than 3 minutes and 30 seconds, the time for a series of operations for denture repair, namely, an operation of mixing a powder material and a liquid material, an operation of placing a paste on a denture, an operation of shaping within the oral cavity, and an operation of taking out the denture from the oral cavity and performing trimming, can be sufficiently secured. Furthermore, it is because when the curing time is longer than 10 minutes, the time required for inserting the denture base lining material inside the oral cavity of the patient is long, and the burden on the patient increases.

(3) Measurement of Complex Modulus Retention Time

Changes over time of the complex modulus were measured using a dynamic viscoelasticity analyzer, CS Rheometer "CVO120HR" (manufactured by Bohlin Instruments, Ltd.). Parallel plates having a diameter of 20 mm were used, and measurement was carried out in an oscillation mode at a frequency of 1 Hz and a measurement temperature of 37 C. A powder material and a liquid material were introduced into a rubber cup at a proportion of powder material (g)/liquid material (ml)=2/1, and the materials were mixed for 20 seconds. Measurement was initiated after one minute from the initiation of mixing. The time required for the complex modulus to change from $10^3$ Pa to $10^4$ Pa and the time required for the complex modulus to change from $10^4$ Pa to $10^6$ Pa were determined, and the times were designated as the respective complex modulus retention times.

Meanwhile, for clinical purpose, the state in which the complex modulus of a paste obtainable by mixing a powder material and a liquid material is about $10^3$ Pa to $10^4$ Pa is appropriate for the stage of inserting into the oral cavity and shaping, and the state in which the complex modulus is about $10^4$ Pa to $10^6$ Pa is appropriate for the stage of taking out of the oral cavity and performing trimming. The respective operations can be carried out with sufficient allowance, and in order to prevent excessive lengthening of the operation time, a viscosity increase pattern that requires 30 to 150 seconds for the complex modulus to change from $10^3$ Pa to $10^4$ Pa and 60 to 360 seconds for the complex modulus to change from $10^4$ Pa to $10^6$ Pa is preferred.

(4) Liquid Material Production Time

The total amount of the (E) radical polymerizable monomer was made constant at 100 g, and the liquid components of the (E) radical polymerizable monomer and (F) aromatic amine compound, and the liquid component of the (G) organic halogen compound that was to be optionally incorporated were weighed in a 200 ml container made of glass. The components were stirred and mixed with a magnetic stirrer. Subsequently, the solid component of the (F) aromatic amine compound and the solid component of the (G) organic halogen compound that was to be optionally incorporated were added into the liquid component, and the point at which the solid components completely dissolved was visually evaluated. The time taken until the solid components were completely dissolved after the addition was designated as the liquid material production time. Meanwhile, production of the liquid material was carried out in a constant temperature chamber at 23 C.

Example 1

(Production of Powder Material)

According to the following formulation, various components were mixed for 3 hours using a rocking mixer, and a powder material was obtained.

(A) Non-Crosslinked Resin Particles

Spherical polyethyl methacrylate particles (average particle size 35 m, weight average molecular weight 500,000) 110 g Spherical polyethyl methacrylate particles (average particle size 70 m, weight average molecular weight 1,000,000) 90 g (B) Organic Peroxide Benzoyl peroxide 2 g (C) Pyrimidinetrione Derivative 1-Cyclohexyl-5-ethylpyrimidinetrione 0.01 g (D) Organometallic Compound Acetylacetone copper(II) 0.0001 g (Production of Liquid Material)

Meanwhile, according to the following formulation, various components were stirred and mixed for 3 hours, and a liquid material was obtained.

(E) Radical Polymerizable Monomer

Acetoacetoxyethyl methacrylate 100 g (F) Aromatic Amine Compound

N,N-dimethyl-p-toluidine 0.6 g p-Tolyldiethanolamine 0.3 g

The surface unpolymerized layer, the curing time, the complex modulus retention time, and the liquid material production time were evaluated using the powder-liquid type denture base lining materials formed from the powder materials and the liquid materials thus obtained.

The compositions of the powder materials and the liquid materials are presented in Table 1 and Table 2, and the test results are presented in Table 5.

Examples 2 to 49

Powder-liquid type denture base lining materials were produced in the same manner as in Example 1, except that the formulations (compositions) of the powder material and the liquid material were changed as shown in Table 1 and Table 2, and the surface unpolymerized layer, the curing time, the complex modulus retention time, and the liquid material production time were evaluated. The test results are presented in Table 5.

Comparative Examples 1 to 15

Powder-liquid type denture base lining materials were produced in the same manner as in Example 1, except that the formulations (compositions) of the powder material and the liquid material were changed as shown in Table 3 and Table 4, and the surface unpolymerized layer, the curing time, the complex modulus retention time, and the liquid material production time were evaluated. The test results are presented in Table 6.

TABLE 1

| | Powder material | | | | | | |
|---|---|---|---|---|---|---|---|
| | (A) Non-crosslinked organic resin | | (B) Organic peroxide | | (C) Pyrimidinetrione derivative | | (D) Organometallic compound | |
| | PEMA1 | PEMA2 | BPO | Perocta H | cHexEt-PTO | cHexMt-PTO | CuAcAc | CuAc |
| Example 1 | 110 | 90 | 2 | | 0.07 | | 0.0001 | |
| Example 2 | 110 | 90 | 2 | | 0.07 | | 0.0001 | |
| Example 3 | 110 | 90 | 2 | | 0.07 | | 0.0001 | |
| Example 4 | 110 | 90 | 2 | | 0.07 | | 0.0001 | |
| Example 5 | 110 | 90 | 2 | | 0.07 | | 0.0001 | |
| Example 6 | 110 | 90 | 2 | | 0.07 | | 0.0001 | |
| Example 7 | 110 | 90 | | 2 | 0.07 | | 0.0001 | |
| Example 8 | 110 | 90 | 2 | | | 0.07 | 0.0001 | |
| Example 9 | 110 | 90 | 2 | | 0.07 | | | 0.0001 |
| Example 10 | 110 | 90 | 2 | | 0.07 | | 0.0001 | |
| Example 11 | 110 | 90 | 2 | | 0.07 | | 0.0001 | |
| Example 12 | 110 | 90 | 2 | | 0.07 | | 0.0001 | |
| Example 13 | 200 | 90 | 2 | | 0.07 | | 0.0001 | |
| Example 14 | 30 | 90 | 2 | | 0.07 | | 0.0001 | |
| Example 15 | 250 | 90 | 2 | | 0.07 | | 0.0001 | |
| Example 16 | 45 | 30 | 2 | | 0.07 | | 0.0001 | |
| Example 17 | 350 | 90 | 2 | | 0.07 | | 0.0001 | |
| Example 18 | 20 | 15 | 2 | | 0.07 | | 0.0001 | |
| Example 19 | 110 | 90 | 3.9 | | 0.14 | | 0.0001 | |
| Example 20 | 110 | 90 | 0.7 | | 0.025 | | 0.0001 | |
| Example 21 | 110 | 90 | 5.5 | | 0.19 | | 0.0001 | |
| Example 22 | 110 | 90 | 0.5 | | 0.018 | | 0.0001 | |
| Example 23 | 110 | 90 | 9 | | 0.3 | | 0.0001 | |
| Example 24 | 110 | 90 | 9 | | 0.81 | | 0.0001 | |
| Example 25 | 110 | 90 | 0.3 | | 0.01 | | 0.0001 | |
| Example 26 | 110 | 90 | 0.3 | | 0.0005 | | 0.0001 | |
| Example 27 | 110 | 90 | 2 | | 0.09 | | 0.0001 | |
| Example 28 | 110 | 90 | 2 | | 0.008 | | 0.0001 | |
| Example 29 | 110 | 90 | 2 | | 0.13 | | 0.0001 | |
| Example 30 | 110 | 90 | 2 | | 0.005 | | 0.0001 | |
| Example 31 | 110 | 90 | 2 | | 0.18 | | 0.0001 | |
| Example 32 | 110 | 90 | 2 | | 0.002 | | 0.0001 | |
| Example 33 | 110 | 90 | 2 | | 0.07 | | 0.018 | |
| Example 34 | 110 | 90 | 2 | | 0.07 | | 0.00004 | |
| Example 35 | 110 | 90 | 2 | | 0.07 | | 0.038 | |
| Example 36 | 110 | 90 | 2 | | 0.07 | | 0.00002 | |
| Example 37 | 110 | 90 | 2 | | 0.07 | | 0.09 | |
| Example 38 | 110 | 90 | 2 | | 0.07 | | 0.000004 | |
| Example 39 | 110 | 90 | 2 | | 0.07 | | 0.0001 | |
| Example 40 | 110 | 90 | 2 | | 0.07 | | 0.0001 | |
| Example 41 | 110 | 90 | 2 | | 0.07 | | 0.0001 | |
| Example 42 | 110 | 90 | 2 | | 0.07 | | 0.0001 | |
| Example 43 | 110 | 90 | 2 | | 0.07 | | 0.0001 | |
| Example 44 | 110 | 90 | 2 | | 0.07 | | 0.0001 | |
| Example 45 | 110 | 90 | 2 | | 0.07 | | 0.0001 | |
| Example 46 | 110 | 90 | 2 | | 0.07 | | 0.0001 | |
| Example 47 | 110 | 90 | 2 | | 0.07 | | 0.0001 | |
| Example 48 | 110 | 90 | 2 | | 0.07 | | 0.0001 | |
| Example 49 | 110 | 90 | 2 | | 0.18 | | 0.0001 | |

TABLE 2

| | Liquid material | | | | | | | | |
|---|---|---|---|---|---|---|---|---|---|
| | (E) (Meth)acrylate-based polymerizable monomer | | | | (F) Aromatic amine compound | | Other components (G) Organic halogen compound | | (C)/(B) mass ratio |
| | AAEM | HPr | ND | MMA | DMPT | DEPT | DLDMACl | DLDMABr | |
| Example 1 | 100 | | | | 0.6 | 0.3 | | | 0.035 |
| Example 2 | | 100 | | | 0.6 | 0.3 | | | 0.035 |
| Example 3 | | | 100 | | 0.6 | 0.3 | | | 0.035 |
| Example 4 | | | | 100 | 0.6 | 0.3 | | | 0.035 |
| Example 5 | 60 | | | 40 | 0.6 | 0.3 | | | 0.035 |
| Example 6 | | 60 | | 40 | 0.6 | 0.3 | | | 0.035 |
| Example 7 | | 60 | | 40 | 0.6 | 0.3 | | | 0.035 |
| Example 8 | | 60 | | 40 | 0.6 | 0.3 | | | 0.035 |
| Example 9 | | 60 | | 40 | 0.6 | 0.3 | | | 0.035 |
| Example 10 | 60 | | | 40 | 0.6 | 0.3 | 0.01 | | 0.035 |
| Example 11 | | 60 | | 40 | 0.6 | 0.3 | 0.01 | | 0.035 |
| Example 12 | | 60 | | 40 | 0.6 | 0.3 | | 0.01 | 0.035 |
| Example 13 | | 60 | | 40 | 0.6 | 0.3 | | | 0.035 |
| Example 14 | | 60 | | 40 | 0.6 | 0.3 | | | 0.035 |
| Example 15 | | 60 | | 40 | 0.6 | 0.3 | | | 0.035 |
| Example 16 | | 60 | | 40 | 0.6 | 0.3 | | | 0.035 |
| Example 17 | | 60 | | 40 | 0.6 | 0.3 | | | 0.035 |
| Example 18 | | 60 | | 40 | 0.6 | 0.3 | | | 0.035 |
| Example 19 | | 60 | | 40 | 0.6 | 0.3 | | | 0.036 |
| Example 20 | | 60 | | 40 | 0.6 | 0.3 | | | 0.036 |
| Example 21 | | 60 | | 40 | 0.6 | 0.3 | | | 0.035 |
| Example 22 | | 60 | | 40 | 0.6 | 0.3 | | | 0.036 |
| Example 23 | | 60 | | 40 | 0.6 | 0.3 | | | 0.033 |
| Example 24 | | 60 | | 40 | 0.6 | 0.3 | | | 0.090 |
| Example 25 | | 60 | | 40 | 0.6 | 0.3 | | | 0.033 |
| Example 26 | | 60 | | 40 | 0.6 | 0.3 | | | 0.002 |
| Example 27 | | 60 | | 40 | 0.6 | 0.3 | | | 0.045 |
| Example 28 | | 60 | | 40 | 0.6 | 0.3 | | | 0.004 |
| Example 29 | | 60 | | 40 | 0.6 | 0.3 | | | 0.065 |
| Example 30 | | 60 | | 40 | 0.6 | 0.3 | | | 0.003 |
| Example 31 | | 60 | | 40 | 0.6 | 0.3 | | | 0.090 |
| Example 32 | | 60 | | 40 | 0.6 | 0.3 | | | 0.001 |
| Example 33 | | 60 | | 40 | 0.6 | 0.3 | | | 0.035 |
| Example 34 | | 60 | | 40 | 0.6 | 0.3 | | | 0.035 |
| Example 35 | | 60 | | 40 | 0.6 | 0.3 | | | 0.035 |
| Example 36 | | 60 | | 40 | 0.6 | 0.3 | | | 0.035 |
| Example 37 | | 60 | | 40 | 0.6 | 0.3 | | | 0.035 |
| Example 38 | | 60 | | 40 | 0.6 | 0.3 | | | 0.035 |
| Example 39 | | 60 | | 40 | 1.3 | 0.6 | | | 0.035 |
| Example 40 | | 60 | | 40 | 0.3 | 0.1 | | | 0.035 |
| Example 41 | | 60 | | 40 | 2 | 0.9 | | | 0.035 |
| Example 42 | | 60 | | 40 | 0.15 | 0.04 | | | 0.035 |
| Example 43 | | 60 | | 40 | 3.6 | 1.3 | | | 0.035 |
| Example 44 | | 60 | | 40 | 0.05 | 0.04 | | | 0.035 |
| Example 45 | | 60 | | 40 | 0.6 | 0.3 | 0.18 | | 0.035 |
| Example 46 | | 60 | | 40 | 0.6 | 0.3 | 0.45 | | 0.035 |
| Example 47 | | | | 100 | 0.6 | 0.3 | 0.18 | | 0.035 |
| Example 48 | | | | 100 | 0.6 | 0.3 | 0.45 | | 0.035 |
| Example 49 | | 60 | | 40 | 0.6 | 0.3 | 0.45 | | 0.090 |

TABLE 3

| | Powder material | | | | | | | |
|---|---|---|---|---|---|---|---|---|
| | (A) Non-crosslinked organic resin | | (B) Organic peroxide | | (C) Pyrimidinetrione derivative | | (D) Organometallic compound | |
| | PEMA1 | PEMA2 | BPO | Perocta H | cHexEt-PTO | cHexMt-PTO | CuAcAc | CuAc |
| Comparative Example 1 | 110 | 90 | 2 | | | | 0.0001 | |
| Comparative Example 2 | 110 | 90 | 2 | | | | 0.0001 | |
| Comparative Example 3 | 110 | 90 | 2 | | | | 0.0001 | |
| Comparative Example 4 | 110 | 90 | 2 | | 1.5 | | 0.0001 | |
| Comparative | 110 | 90 | 2 | | 1.5 | | 0.0001 | |

TABLE 3-continued

| | Powder material | | | | | | | |
|---|---|---|---|---|---|---|---|---|
| | (A) Non-crosslinked organic resin | | (B) Organic peroxide | | (C) Pyrimidinetrione derivative | | (D) Organometallic compound | |
| | PEMA1 | PEMA2 | BPO | Perocta H | cHexEt-PTO | cHexMt-PTO | CuAcAc | CuAc |
| Example 5 | | | | | | | | |
| Comparative Example 6 | 110 | 90 | 2 | | 0.0001 | | 0.0001 | |
| Comparative Example 7 | | | 2 | | 0.07 | | 0.0001 | |
| Comparative Example 8 | 110 | 90 | | | 0.07 | | 0.0001 | |
| Comparative Example 9 | 110 | 90 | 2 | | 0.07 | | | |
| Comparative Example 10 | 110 | 90 | 2 | | 0.07 | | 0.0001 | |
| Comparative Example 11 | 110 | 90 | 2 | | 0.07 | | 0.0001 | |
| Comparative Example 12 | 110 | 90 | | | 3.0 | | 0.002 | |
| Comparative Example 13 | 110 | 90 | | | 3.0 | | 0.002 | |
| Comparative Example 14 | 110 | 90 | 0.2 | | 3.0 | | 0.004 | |
| Comparative Example 15 | 110 | 90 | 0.2 | | 3.0 | | 0.004 | |

TABLE 4

| | Liquid material | | | | | | | | | |
|---|---|---|---|---|---|---|---|---|---|---|
| | (E) (Meth)acrylate-based polymerizable monomer | | | | (F) Aromatic amine compound | | Other components | | | (C)/(B) mass ratio |
| | | | | | | | (G) Organic halogen compound | | | |
| | AAEM | HPr ND | MMA | | DMPT | DEPT | DLDMACl | DLDMABr | α-MSD | |
| Comparative Example 1 | | 60 | 40 | | 0.6 | 0.3 | | | | — |
| Comparative Example 2 | | 60 | 40 | | 0.6 | 0.3 | 0.01 | | | — |
| Comparative Example 3 | | 60 | 40 | | 0.6 | 0.3 | 0.01 | | | — |
| Comparative Example 4 | 60 | | 40 | | 0.6 | 0.3 | | | | 0.75 |
| Comparative Example 5 | | 60 | 40 | | 0.6 | 0.3 | 0.7 | | | 0.75 |
| Comparative Example 6 | | 60 | 40 | | 0.6 | 0.3 | | | | 0.00005 |
| Comparative Example 7 | | 60 | 40 | | 0.6 | 0.3 | | | | 0.035 |
| Comparative Example 8 | | 60 | 40 | | 0.6 | 0.3 | | | | — |
| Comparative Example 9 | | 60 | 40 | | 0.6 | 0.3 | | | | 0.035 |
| Comparative Example 10 | | | | | 0.6 | 0.3 | | | | 0.035 |
| Comparative Example 11 | | 60 | 40 | | | | | | | 0.035 |
| Comparative Example 12 | | 60 | 40 | | 2 | 0.3 | | | | — |
| Comparative Example 13 | | 60 | 40 | | | 0.3 | | | 0.25 | — |
| Comparative Example 14 | | 60 | 40 | | | 0.2 | | 0.2 | | 15 |
| Comparative Example 15 | | 60 | 40 | | | 0.2 | | 7 | | 15 |

TABLE 5

| | Surface unpolymerized layer (μm) | Curing time | Complex modulus retention time (seconds) $10^3$ Pa~$10^4$ Pa | Complex modulus retention time (seconds) $10^4$ Pa~$10^6$ Pa | Liquid material production time (minutes) |
|---|---|---|---|---|---|
| Example 1 | 163 | 4'50" | 37 | 101 | 35 |
| Example 2 | 160 | 4'43" | 39 | 106 | 30 |
| Example 3 | 144 | 4'40" | 35 | 88 | 40 |
| Example 4 | 120 | 4'00" | 31 | 70 | 25 |
| Example 5 | 155 | 4'45" | 38 | 94 | 30 |
| Example 6 | 150 | 4'55" | 36 | 98 | 35 |
| Example 7 | 158 | 4'47" | 40 | 87 | 35 |
| Example 8 | 160 | 4'43" | 38 | 90 | 35 |
| Example 9 | 162 | 4'41" | 37 | 99 | 35 |
| Example 10 | 135 | 4'47" | 34 | 80 | 37 |
| Example 11 | 137 | 4'44" | 40 | 82 | 37 |
| Example 12 | 146 | 4'45" | 45 | 102 | 35 |
| Example 13 | 155 | 5'00" | 37 | 77 | 35 |
| Example 14 | 160 | 4'23" | 51 | 90 | 35 |
| Example 15 | 156 | 5'12" | 34 | 81 | 35 |
| Example 16 | 149 | 4'11" | 58 | 80 | 35 |
| Example 17 | 154 | 5'30" | 30 | 90 | 35 |
| Example 18 | 152 | 4'06" | 62 | 66 | 35 |
| Example 19 | 151 | 4'13" | 37 | 80 | 35 |
| Example 20 | 154 | 5'37" | 42 | 92 | 35 |
| Example 21 | 155 | 5'02" | 38 | 72 | 35 |
| Example 22 | 157 | 5'59" | 49 | 100 | 35 |
| Example 23 | 149 | 3'49" | 35 | 69 | 35 |
| Example 24 | 121 | 3'35" | 35 | 65 | 35 |
| Example 25 | 155 | 6'20" | 55 | 112 | 35 |
| Example 26 | 167 | 6'22" | 55 | 112 | 35 |
| Example 27 | 140 | 4'37" | 37 | 77 | 35 |
| Example 28 | 153 | 5'55" | 42 | 82 | 35 |
| Example 29 | 155 | 4'30" | 38 | 70 | 35 |
| Example 30 | 157 | 5'59" | 47 | 89 | 35 |
| Example 31 | 153 | 4'14" | 35 | 66 | 35 |
| Example 32 | 158 | 6'02" | 50 | 93 | 35 |
| Example 33 | 140 | 4'41" | 40 | 87 | 35 |
| Example 34 | 156 | 4'51" | 36 | 90 | 35 |
| Example 35 | 145 | 4'38" | 41 | 85 | 35 |
| Example 36 | 159 | 4'55" | 39 | 83 | 35 |
| Example 37 | 147 | 4'34" | 39 | 80 | 35 |
| Example 38 | 169 | 4'57" | 42 | 77 | 35 |
| Example 39 | 156 | 4'35" | 47 | 90 | 37 |
| Example 40 | 153 | 5'00" | 46 | 80 | 33 |
| Example 41 | 159 | 4'26" | 44 | 77 | 39 |
| Example 42 | 157 | 5'10" | 51 | 96 | 20 |
| Example 43 | 152 | 4'10" | 39 | 74 | 41 |
| Example 44 | 155 | 5'50" | 55 | 110 | 15 |
| Example 45 | 130 | 4'03" | 45 | 85 | 43 |
| Example 46 | 134 | 3'50" | 41 | 81 | 50 |
| Example 47 | 111 | 3'52" | 37 | 71 | 35 |
| Example 48 | 114 | 3'44" | 34 | 78 | 38 |
| Example 49 | 117 | 3'40" | 32 | 66 | 50 |

TABLE 6

| | Surface unpolymerized layer (μm) | Curing time | Complex modulus retention time (seconds) $10^3$ Pa~$10^4$ Pa | Complex modulus retention time (seconds) $10^4$ Pa~$10^6$ Pa | Liquid material production time (minutes) |
|---|---|---|---|---|---|
| Comparative Example 1 | 221 | 4'54" | 37 | 98 | 35 |
| Comparative Example 2 | 199 | 4'37" | 46 | 86 | 37 |
| Comparative Example 3 | 201 | 4'43" | 50 | 67 | 37 |
| Comparative Example 4 | 116 | 3'14" | 36 | 50 | 35 |
| Comparative Example 5 | 105 | 3'07" | 34 | 47 | 60 |
| Comparative Example 6 | 190 | 4'52" | 37 | 100 | 35 |
| Comparative Example 7 | (Not cured) | (Not cured) | (Not cured) | (Not cured) | 35 |

TABLE 6-continued

| | Surface unpolymerized layer (μm) | Curing time | Complex modulus retention time (seconds) $10^3$ Pa~$10^4$ Pa | Complex modulus retention time (seconds) $10^4$ Pa~$10^6$ Pa | Liquid material production time (minutes) |
|---|---|---|---|---|---|
| Comparative Example 8 | (Not cured) | (Not cured) | 47 | (Not cured) | 35 |
| Comparative Example 9 | 211 | 4'51" | 41 | 96 | 35 |
| Comparative Example 10 | (Not cured) | (Not cured) | 26 | (Not cured) | 45 |
| Comparative Example 11 | (Not cured) | (Not cured) | 46 | (Not cured) | 0 |
| Comparative Example 12 | 98 | 2'30" | 27 | 40 | 50 |
| Comparative Example 13 | 100 | 3'05" | 30 | 43 | 41 |
| Comparative Example 14 | 103 | 3'05" | 32 | 43 | 39 |
| Comparative Example 15 | 112 | 3'35" | 35 | 57 | 39 |

In Examples 1 to 49, the various components were mixed so as to satisfy the configuration disclosed in the present invention, and in all of the cases, the surface unpolymerized layer was small, while the curing time and the complex modulus retention time exhibited desired viscosity increases as required from a denture base lining material. Furthermore, the liquid material production time was also short, and satisfactory liquid productivity was exhibited.

In contrast, Comparative Example 1 was a case in which the (C) pyrimidinetrione derivative was not incorporated, and the surface unpolymerized layer was increased to a large extent. Comparative Examples 2 and 3 were cases in which the (G) organic halogen compound was incorporated, and the (C) pyrimidinetrione derivative was not incorporated, and similarly, the surface unpolymerized layer was increased to a large extent.

Comparative Example 4 was a case in which the (C) pyrimidinetrione derivative was incorporated in excess. The surface unpolymerized layer was diminished; however, the curing time was short, the complex modulus retention time was short, and a viscosity increase as required from a denture base lining material was not obtained.

Comparative Example 5 was a case in which the (C) pyrimidinetrione derivative and the (G) organic halogen compound were incorporated in excess. The surface unpolymerized layer was diminished; however, the curing time was short, the complex modulus retention time was short, and a viscosity increase as required from a denture base lining material was not obtained. Furthermore, since the (G) organic halogen compound having poor solubility in a radical polymerizable monomer was incorporated in excess, liquid material production required a long time.

Comparative Example 6 was a case in which the amount of incorporation of the (C) pyrimidinetrione derivative was small, and the surface unpolymerized layer was large. Comparative Example 7 was a case in which the (A) non-crosslinked resin particles were not incorporated; however, since the main component of the powder material was not incorporated, the lining material did not cure.

Comparative Example 8 was a case in which the (B) organic peroxide was not incorporated, and since the main catalyst system of the present invention was not incorporated, the lining material did not cure. Comparative Example 9 was a case in which the (D) organometallic compound was not incorporated, and since the catalytic ability of the pyrimidinetrione derivative was not exhibited, the surface unpolymerized layer was large. Comparative Example 10 was a case in which the (E) radical polymerizable monomer was not incorporated, and since the main component of the liquid was not incorporated, the lining material did not cure. Comparative Example 11 was a case in which the (F) aromatic amine compound was not incorporated, and since the catalytic ability of the organic peroxide was not exhibited, the lining material did not cure.

Comparative Example 12 was a case in which the (B) organic peroxide was not incorporated, the (C) pyrimidinetrione derivative was incorporated in excess, and the (G) organic halogen compound was incorporated. Since the pyrimidinetrione-based polymerization initiator worked as a main catalyst, the surface unpolymerized layer was diminished; however, the curing time and the complex modulus retention time were noticeably short.

Comparative Example 13 was a case in which the (B) organic peroxide and the (F) aromatic amine compound were not incorporated, the (C) pyrimidinetrione derivative was incorporated in excess, and 2,4-diphenyl-4-methyl-1-pentene was incorporated as a polymerization regulating agent. Since the pyrimidinetrione-based polymerization initiator worked as a main catalyst, the surface unpolymerized layer was diminished. 2,4-Diphenyl-4-methyl-1-pentene delayed the curing time; however, since the pyrimidinetrione-based polymerization initiator worked as a main catalyst, the curing time and the complex modulus retention time were short as for a denture base lining material.

Comparative Example 14 was a case in which the (F) aromatic amine compound was not included, the (B) organic oxide was incorporated in the lower limit amount, the (C) pyrimidinetrione derivative was incorporated in excess, and 2,4-diphenyl-4-methyl-1-pentene was incorporated as a polymerization regulating agent. Since the pyrimidinetrione polymerization initiator worked as a main catalyst, the surface unpolymerized layer was diminished; however, the curing time and the complex modulus retention time were short. Comparative Example 15 had a configuration similar to that of Comparative Example 14 and was a case in which 2,4-diphenyl-4-methyl-1-pentene was incorporated in a large amount. The surface unpolymerized layer was diminished, and the curing time was also a satisfactory curing time as for a denture base lining material. However, the complex modulus retention time was short, and a desired viscosity increase as required from a denture base lining material was not obtained.

The invention claimed is:

1. A powder-liquid type denture base lining material, comprising:
    a powder material including:
    (A) a non-crosslinked resin particles,
    (B) an organic peroxide,
    (C) a pyrimidinetrione derivative, and
    (D) an organometallic compound; and
    a liquid material including:
    (E) a radical polymerizable monomer, and
    (F) an aromatic amine compound,
    wherein
        the (C) pyrimidinetrione derivative is included in an amount of 0.0002 to 1.0 part by mass with respect to 100 parts by mass of the (E) radical polymerizable monomer,
        a mass ratio of the (C) pyrimidinetrione derivative to the (B) organic peroxide is 0.001 to 0.1, and
        the liquid material does not incorporate (G) an organic halogen compound.

2. The powder-liquid type denture base lining material according to claim 1, wherein the (B) organic peroxide is included in an amount of 0.2 to 10 parts by mass, and the (D) organometallic compound is included in an amount of 0.000002 to 0.1 part by mass, with respect to 100 parts by mass of the (E) radical polymerizable monomer.

3. The powder-liquid type denture base lining material according to claim 1, wherein the (E) radical polymerizable monomer has a molecular weight of 150 or more.

4. The powder-liquid type denture base lining material according to claim 1, wherein the (C) pyrimidinetrione derivative is a compound represented by the following General Formula (1):

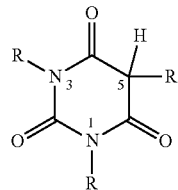

(1)

wherein under the condition that all of three R's are not hydrogen atoms, three R's each represent a hydrogen atom, an alkyl group having 1 to 8 carbon atoms, or a cycloalkyl group having 3 to 8 carbon atoms.

* * * * *